United States Patent
Yang et al.

(10) Patent No.: US 11,097,008 B2
(45) Date of Patent: *Aug. 24, 2021

(54) COLLOIDAL MICROCRYSTALLINE CELLULOSE COMPOSITIONS, THEIR PREPARATION AND PRODUCTS

(71) Applicant: DUPONT NUTRITION USA, INC., Wilmington, DE (US)

(72) Inventors: Hong Yang, Newark, DE (US); Jeremy Ondov, New York, NY (US); Toh Mei Yan Joyce, Langhorne, PA (US); Aaron Chip Venables, Yardley, PA (US); Simon Eustace, Lincoln University, PA (US); Kevin Stokes, Hamilton Square, NJ (US)

(73) Assignee: DUPONT NUTRITION USA, INC., Wilmington, DE (US)

(*) Notice: Subject to any disclaimer, the term of this patent is extended or adjusted under 35 U.S.C. 154(b) by 202 days.

This patent is subject to a terminal disclaimer.

(21) Appl. No.: 16/013,122

(22) Filed: Jun. 20, 2018

(65) Prior Publication Data

US 2018/0369394 A1 Dec. 27, 2018

Related U.S. Application Data

(60) Provisional application No. 62/524,115, filed on Jun. 23, 2017.

(51) Int. Cl.

| | |
|---|---|
| A61K 47/38 | (2006.01) |
| A61K 47/36 | (2006.01) |
| A61K 9/107 | (2006.01) |
| A61K 8/04 | (2006.01) |
| A61K 8/73 | (2006.01) |
| A23G 1/56 | (2006.01) |
| A23L 29/262 | (2016.01) |
| A23G 1/00 | (2006.01) |
| A61K 8/02 | (2006.01) |

(52) U.S. Cl.
CPC ............ *A61K 47/38* (2013.01); *A23G 1/00* (2013.01); *A23G 1/56* (2013.01); *A23L 29/262* (2016.08); *A61K 8/0241* (2013.01); *A61K 8/04* (2013.01); *A61K 8/731* (2013.01); *A61K 8/733* (2013.01); *A61K 9/107* (2013.01); *A61K 47/36* (2013.01); *A23V 2002/00* (2013.01); *A61K 2800/10* (2013.01); *A61K 2800/412* (2013.01); *A61K 2800/624* (2013.01)

(58) Field of Classification Search
None
See application file for complete search history.

(56) References Cited

U.S. PATENT DOCUMENTS

| | | | |
|---|---|---|---|
| 3,539,365 | A | 11/1970 | Durand et al. |
| 3,573,058 | A | 3/1971 | Tiemstra et al. |
| 5,209,942 | A | 5/1993 | Bauer |
| 7,462,232 | B2 | 12/2008 | Tuason et al. |
| 7,879,382 | B2 | 2/2011 | Tuason et al. |
| 9,828,493 | B2 | 11/2017 | Tan et al. |
| 2005/0233046 | A1 | 10/2005 | Krawczyk et al. |
| 2006/0096500 | A1 | 5/2006 | Tuason |
| 2011/0151097 | A1 | 6/2011 | Tuason et al. |
| 2013/0064953 | A1 | 3/2013 | Bache et al. |
| 2014/0370180 | A1 | 12/2014 | Tan |

FOREIGN PATENT DOCUMENTS

| | | |
|---|---|---|
| EP | 2401325 B1 | 5/2010 |
| WO | 9014017 A1 | 11/1990 |

OTHER PUBLICATIONS

Imeson, Alan, "Food Stabilizers, Thickeners and Gelling Agents", FMC BioPolymer; UK, 2010.

*Primary Examiner* — Layla D Berry

(57) ABSTRACT

The present invention is directed colloidal microcrystalline compositions, particularly for suspending particles in low viscosity fluids, produced by co-attrition of a mixture of microcrystalline cellulose and at least a polysaccharide in the presence of acidic attrition aid; their preparation; and, products made therewith.

12 Claims, No Drawings

COLLOIDAL MICROCRYSTALLINE CELLULOSE COMPOSITIONS, THEIR PREPARATION AND PRODUCTS

FIELD OF THE INVENTION

The present invention is directed to colloidal microcrystalline compositions, particularly for suspending particles in low viscosity fluids, produced by co-attrition of a mixture of microcrystalline cellulose and at least one polysaccharide in the presence of acidic attrition aid; their preparation; and, products made therewith.

BACKGROUND OF THE INVENTION

Microcrystalline cellulose, also known and referred to herein as "MCC", is hydrolyzed cellulose. MCC powders and gels are commonly used in the food industry to enhance the properties or attributes of a final food product. For example, MCC has been used as a binder and stabilizer in a wide variety of consumable products such as food applications, including in beverages, as a gelling agent, a thickener, a fat substitute, and/or non-caloric filler, and as a suspension stabilizer and/or texturizer. MCC has also been used as a binder and disintegrant in pharmaceutical tablets, as a suspending agent in liquid pharmaceutical formulations, and as a binder, disintegrant, and processing aid, in industrial applications, in household products such as detergents and/or bleach tablets, in agricultural formulations, and in personal care products such as dentifrices and cosmetics. An important application for colloidal MCC is stabilization of suspensions, e.g., suspensions of solid particles in low viscosity liquids; and, more specifically, suspension of solids in milk, e.g., cocoa particles in chocolate milk.

MCC may be modified for the above-mentioned uses by subjecting hydrolyzed MCC aggregated crystallites, in the form of a high solids aqueous mixture, commonly known as "wetcake", to an attrition process, e.g., extrusion, that substantially subdivides the aggregated cellulose crystallites into more finely divided crystallite particles. To prevent hornification, a protective hydrocolloid may be added before, during, or following attrition, but before drying. The protective hydrocolloid, wholly or partially, screens out the hydrogen bonds or other attractive forces between the smaller sized particles to provide a readily dispersible powder. Colloidal MCC will typically form stable suspensions with little to no settling of the dispersed solids. Carboxymethyl cellulose is a common hydrocolloid used for these purposes (see for example U.S. Pat. No. 3,539,365 (Durand et al.) and the colloidal MCC products sold under the brand names AVICEL® and GELSTAR® by FMC Corporation. Many other hydrocolloids have been tried to co-process with MCC, such as starch, in U.S. Pat. App. 2011/0151097 (Tuason et al.)

One of the disadvantages of colloidal MCC having carboxymethyl cellulose of a viscosity of at least 100 cP and a degree of substitution of at least 0.95 is that they may be too 'slippery' to provide effective co-attrition of wetcake. Less than satisfactory attrition of the MCC particles can have a deleterious effect on the functionality of a MCC stabilizer. As a result, attempts have been made to solve this problem by using an attrition aid, e.g., a salt of multivalent ions, to increase friction among the particles in the wetcake to make attrition more effective. For example, see: U.S. Pat. Nos. 7,879,382 and 7,462,232. Other approaches have been taken to improve attrition of MCC/hydrocolloid compositions, for example, see: US 2005/0233046; US 2011/0151097; and WO 2010/136157.

Because of the nature of it's processing, CMC has recently come under attack for not being a "clean label" component, although still considered safe by regulatory authorities. As such, attempts have been made to replace the CMC with polysaccharides from various plant sources. This has proved challenging, however since each polysaccharide has its own unique structure and it has been difficult to predict their respective functionalities. Many polysaccharides have not been found effective for making dispersion stable MCCs at least partially due to a lack of transfer of sufficient mechanical force to the MCC aggregates and polysaccharides during attrition. One attempt to mitigate the problem has been to use multivalent salts such as calcium chloride (see for example U.S. Pat. No. 7,462,232 B2, to Tuason et al). However, under the specific conditions described by Tuason (cool/ambient dispersion of Avicel® AC4125 to reduce due to the gelling potential resulting from interaction of guluronate groups in alginate with calcium ions in the milk) a sequestrant was needed.

There is a need therefore to devise a colloidal MCC composition useful for the stabilization of low viscosity liquids that may be effectively attrited without the addition of multivalent ions and avoiding the presence of CMC.

Applicants have met the stated need, by providing a co-attrited colloidal composition that can be effectively attrited without carboxymethyl cellulose and/or multi-valent ions; and, can be dispersed easily in consumable products such as food, beverage, pharmaceutical, industrial, and many other products; including, cool/ambient milk products, e.g., chocolate milk, without the use of sequestrant.

SUMMARY OF THE INVENTION

The present invention provides a colloidal MCC composition, substantially free of multi-valent ions comprising: MCC particles which are at least partially coated with at least one polysaccharide, and an acid or salt, wherein the salt is substantially free of multivalent ions and wherein the $D_{50}$ of at least 19% by volume of the MCC particles is about 0.110 microns.

In alternative embodiments the $D_{50}$ of at least 25% by volume or 40% by volume or in some case at least 70% by volume of the MCC particles in the composition of the invention is about 0.110 microns.

In another aspect the invention provides a colloidal composition comprising MCC particles which comprise between about 40-91.99% wt. of the composition; at least one polysaccharide which comprises between about 8-50% wt. of the composition and an attrition agent which comprises between about 0.01-10% wt. of the composition wherein the $D_{50}$ of at least 19% by volume of the MCC particles is about 0.110 microns.

The polysaccharides useful in this invention include acidic sugar residues preferably in the main polymer chain. The useful acid residues include galacturonic acid, glucuronic acid, mannuronic acid and guluronic acid, and, preferred polysaccharides include at least one of alginate, karaya, and may optionally include carboxymethyl cellulose.

Among acids useful in this invention are those that reduce the pH of the wetcake to 4.5 or less and that are otherwise compatible with the intended product and its use. In some applications, a pH of less than 3.0 may be required depending on the pH of the starting materials. For ingestible products, some acids that are generally recognized as safe include formic acid, acetic acid, propionic acid, butyric acid, valeric acid, caproic acid, oxalic acid, lactic acid, malic acid, citric acid, benzoic acid, carbonic acid, tartaric acid, hydrochloric acid, nitric acid, phosphoric acid, sulfuric acid, boric acid, hydrofluoric acid, hydrobromic acid, and mixtures thereof.

The present invention further provides a method for preparing an attrited MCC composition comprising: a) providing MCC particles; b) providing an acid; c) providing at least one a polysaccharide; co-attriting the MCC particles, the acid and the at least one polysaccharide to produce an attrited MCC composition, wherein the acid is provided in an amount effective to lower the pH of the composition to 4.5 or less, and wherein the MCC particles are at least partially coated with the at least one polysaccharide; and wherein the $D_{50}$ of at least 19% by volume of the MCC particles is about 0.110 microns. This method is effective for preparing all of the colloidal MCC compositions disclosed herein.

The present invention also provides co-attrited MCC compositions for providing Suspension Stability, and Dispersion Stability. For example the invention provides a consumable product comprising MCC particles wherein the particle attain Suspension Stability as defined herein. Similarly the invention provides a consumable product comprising MCC particles wherein the particles attain Dispersion Stability as defined herein.

DETAILED DESCRIPTION OF THE INVENTION

Unless otherwise specified all references cited herein are incorporated by reference in their entirety.

The following definitions may be used for the interpretation of the claims and specification:

As used herein, the terms "comprises," "comprising," "includes," "including," "has," "having," "contains" or "containing," or any other variation thereof, are intended to cover a non exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "$D_{50}$" as used in relation to particle size distribution denotes the diameter of the particle that 50% of a sample's volume is smaller than, and 50% of a sample's volume is larger than.

As used herein, "aggregated MCC" means MCC prior to attrition; "attrited MCC" means MCC after attrition; and, "colloidal MCC" means MCC, after attrition in which the $D_{50}$ of at least 19% by volume of the MCC particles is about 0.110 microns as measured by the static light scattering.

The term "attrition aid" or "attrition agent" will be used interchangeably and means a reagent added to an aggregated MCC composition that facilitates attrition, particularly extrusion.

The term Dispersion Stability or Dispersion Stable, as used herein, means that the coated MCC particles themselves disperse uniformly in liquids, e.g., an aqueous medium, without vigorous agitation forming a suspension having a homogenous appearance without significant separating, aggregating or settling of the particles.

The term Suspension Stability, as used herein, means that when the coated MCC particles are dispersed in a liquid, e.g., aqueous medium, milk, etc., containing insoluble components other than the MCC particles, e.g., cocoa, calcium, etc., those particles are effectively suspended forming a stabilized suspension having a homogenous appearance without significant separating, aggregating, or settling of the insoluble particles.

The term "polysaccharide" means a carbohydrate containing more than three monosaccharide units per molecule, the units being attached to each other in the manner of acetals, and therefore capable of hydrolysis by acids or enzymes to monosaccharides. Preferred polysaccharides of the invention are those that contain acidic residues.

The terms "attrited" and "attrition" are used interchangeably to mean a process that effectively reduces the size of at least some if not all of the particles to a colloidal size.

The term "co-attrition" refers to application of high shear forces to an admixture of the MCC and at least one polysaccharide. Suitable attrition conditions may be obtained, for example, by co-extruding, milling, or kneading.

The term "consumable product" means a food, beverage, nutraceutical or pharmaceutical product that is formulated for human or animal consumption.

The present invention encompasses colloidal MCC compositions prepared from a high solids content mixture, e.g., a wetcake that is comprised of MCC aggregate, at least one polysaccharide, water, and an acid, in an amount effective to lower the pH of the wetcake to 4.5 or less. The mixture may be attrited, e.g., extruded, to subdivide the MCC aggregates to 'colloidal MCC' wherein the $D_{50}$ of at least 19% by volume of the MCC particles is about 0.110 microns. Thereafter, the subdivided, coated colloidal MCC may be dried with any suitable technique, e.g., spray dried, drum dried, fluid bed dried, and flash dried, to form a dispersible powder.

Microcrystalline Cellulose

The present invention makes use of hydrolyzed microcrystalline cellulose. Microcrystalline cellulose (MCC) is a white, odorless, tasteless, relatively free flowing, crystalline powder that is virtually free from organic and inorganic contaminants. It is a purified, partially depolymerized cellulose obtained by subjecting alpha cellulose obtained as a pulp from fibrous plant material to hydrolytic degradation typically with mineral acids. It is a highly crystalline particulate cellulose consisting primarily of crystalline aggregates which are obtained by removing amorphous regions (or paracrystalline regions) of a cellulosic fibril. MCC is used in a variety of applications including foods, nutraceuticals, pharmaceuticals and cosmetics.

Any microcrystalline cellulose may be employed in the compositions of the present invention. Suitable feedstocks include, for example, wood pulp such as bleached sulfite and sulfate pulps, corn husks, bagasse, straw, cotton, cotton linters, flax, kemp, ramie, fermented cellulose, etc. Microcrystalline cellulose may be produced by treating a source of cellulose, preferably alpha cellulose in the form of pulp from fibrous plant materials, with a mineral acid, preferably hydrochloric acid. The acid selectively attacks the less ordered regions of the cellulose polymer chain thereby exposing and freeing the crystalline sites which form crystallite aggregates which constitute the microcrystalline cellulose. These are then separated from the reaction mixture, and washed to remove degraded by-products. The resulting wet mass, generally containing 40 to 75 percent moisture, is referred to in the art by several names, including hydrolyzed cellulose, hydrolyzed cellulose wetcake, level-off DP cellulose, microcrystalline cellulose wetcake or simply wetcake. Preferably, the aggregated MCC is acid hydrolyzed and 25-60% wt. in water.

When the wetcake is dried and freed of water the resulting product, microcrystalline cellulose, is a white, odorless, tasteless, relatively free-flowing powder, insoluble in water, organic solvents, dilute alkalis and acids. For a description of microcrystalline cellulose and its manufacture see U.S. Pat. No. 2,978,446. The patent describes its use as a pharmaceutical excipient, particularly as a binder, disintegrant, flow aid, and/or filler for preparation of compressed pharmaceutical tablets.

Polysaccharides

In one aspect of the invention the hydrolyzed MCC is coattrited with at least one polysaccharide. Polysaccharides useful in this invention increase energy transfer to a wetcake in the presence of acid, e.g., at pHs 4.5 or less. Preferred in the present invention are those polysaccharides containing acidic sugar residues such as for example, galacturonic acid, glucuronic acid, mannuronic acid and/or guluronic acid residues. It is particularly preferred where those residues reside on a main polymer chain in the polysaccharide. The polysaccharides of the invention may be isolated from a multiplicity of plant exudates as from for example gum arabic, gum ghatti, gum karaya, gum tragacanth; plant seeds such as starches, locust bean gum, guar gum, psyllium seed gum, quince seed gum; plant roots such as konjac; seaweed polysaccharides (e.g. agar, carrageenan, furcellaran, alginate and derivatives there of such as propylene glycol alginate and monovalent salts of alginates), microbial and/or fermentation products such as dextran, xanthan gum and combinations thereof.

Preferred herein are alginate, karaya. Optionally the polysaccharide may be carboxymethyl cellulose. Particularly preferred is alginate which is a salt of alginic acid and a linear copolymer with homopolymeric blocks of mannuronic acids and guluronic acid residues.

Polysaccharides useful in this invention increase energy transfer to a wetcake in the presence of acid, e.g., at pHs 4.5 or less. The polysaccharides include acidic groups, preferably, galacturonic acid, glucuronic acid, mannuronic acid and/or guluronic acid residues, positioned in their main polymer chain, e.g., alginate, karaya where optionally the polysaccharide may be carboxymethyl cellulose. This polysaccharide is selected to be compatible with the intended product requirements, e.g., generally recognized as safe for ingestible products.

Acids

The present invention uses an acid in the co-attrition process. Suitable acids include but are not limited to formic acid, acetic acid, propionic acid, butyric acid, valeric acid, tartaric acid, caproic acid, oxalic acid, lactic acid, malic acid, citric acid, benzoic acid, carbonic acid, hydrochloric acid, nitric acid, phosphoric acid, sulfuric acid, boric acid, hydrofluoric acid, and hydrobromic acid. Preferred herein are organic and inorganic acids. Such acids capable of reducing the pH of wetcake to 4.5 or less and otherwise compatible with the intended product, e.g., generally recognized as safe for ingestible products. Preferred acids include: malic acid, citric acid, tartaric acid, HCl, nitric acid, phosphoric acid; and, more preferred are citric acid, HCl, nitric acid, phosphoric acid, and mixtures thereof.

Attrition Methods

The hydrolyzed MCC and polysaccharide are typically co-attrited in the presence of the acid to form the co-attrited composition wherein the MCC particles are at least partially coated by the polysaccharide. Attrition methods are common and well known in the art (see for example US Patent Application 2013/0090391 and U.S. Pat. No. 9,828,493 which are hereby incorporated by reference). The methods include preparing an aggregate microcrystalline cellulose of between about 25% and 60% wt. solids; further including a polysaccharide, and an attrition agent comprising an acid or salt, (wherein the salt is substantially free of multivalent ions) thereof; wherein the $D_{50}$ of at least 19% by volume of the MCC particles is about 0.110 microns. The composition is 40-91.99% wt. MCC, 8-50% wt. polysaccharide and 0.01-10% by wt. attrition agent.

Attrition may be accomplished by extrusion, for example or with other mechanical devices including, e.g., refiners, planetary mixers, colloidal mills, beat mills, kneaders, and grinders that can provide effective shearing force. However, as particle size is reduced, the individual particles tend to agglomerate or hornify upon drying, a result that is undesirable because it impedes dispersion of the individual particles. Consequently in some embodiments, the D50 of at least about 20%, or 35% or 30% or 35% of 40% or 45% of 50% of 55% or 60% or 65% or 70% by volume of the MCC particles is about 0.110 microns, or may be from about 0.110 microns to about 0.70 microns or from about 0.110 microns to about 0.65 microns or from about 0.110 microns to about 0.50 microns.

The extrudate can be dried or be dispersed in water to form a slurry. The slurry can be homogenized and dried, preferably spray dried, Drying processes other than spray drying include, for example, fluidized bed drying, drum drying, bulk drying, and flash drying. Dry particles formed from the spray drying can be reconstituted in a desired aqueous medium or solution to form the compositions, edible food products, pharmaceutical applications, and industrial applications described herein, Effectiveness of the attrition can be assessed through measuring the viscosity of the mixture of MCC and polysaccharide through the attrition as compared to the viscosity of the mixture of MCC and polysaccharide without through the attrition. During an attrition, strong mechanical shear forces not only break down aggregated MCC particles but also introduce a mixing action to spread polysaccharide molecules around the reduced MCC particles. Furthermore, water molecules in between of MCC particles and polysaccharide are squeezed out to bring MCC particles and polysaccharide into a close contact. Eventually, certain portion on the surface of MCC particles is forced to bond certain segment of polysaccharide chains through molecular interaction force, for instance, the hydrogen bond. In such a manner, the MCC particles act as the node points of polysaccharide network, like crosslinking of polysaccharide, leading to the increase in the viscosity of the mixture of MCC particles and polysaccharide.

Mechanism of Action.

Without wishing to be bound by any particular theory or mode of action for the subject invention, it is believed that the acid reduces the solubility of the polysaccharide during attrition, which increases the transfer of mechanical energy to the wetcake, making attrition more effective so that the MCC particles are more efficiently subdivided to colloidal sizes and at least partially coated without the use of salts of multi-valent metals or carboxymethyl cellulose. The resulting colloidal MCC is easily dispersed in aqueous systems and effectively stabilizes suspensions including in an aqueous medium, e.g., cool milk.

Applications

The colloidal MCC compositions of the invention may be used in a variety of are suitable for a wide variety of food, pharmaceutical, nutraceutical and industrial applications including in cosmetic products, personal care products, consumer products, agricultural products, or in chemical formulations and in paint, polymer formulations.

Some examples in pharmaceutical applications include liquid suspending agents and/or emulsions for drugs; nasal sprays for drug delivery where the colloidal MCC gives increased residence and bioavailability; controlled release agents in pharmaceutical applications; and re-constitutable powders which are dry powders mixtures containing drugs which can be made into a suspension by adding water and shaking by-hand; topical drug applications, and various foams, creams, lotions for medical uses, including compositions for oral care such as toothpaste, mouthwash and the like. One particular example is a suspension of benzoyl peroxide or similar agents, which requires the stability of the colloidal MCC against oxidizing agent over time. Other examples include pharmaceutical suspensions (or re-constituable powders) which are acidic or with high ionic strength.

Some examples in nutraceutical applications include delivery systems for various nutraceutical ingredients and dietary supplements. Examples in industrial applications include various suspensions, thickeners, which can be used in foams, creams, lotions and sun-screens for personal care applications; suspending agents, which can be used with pigments and fillers in ceramics, or used in colorants, optical brighteners, cosmetics, and oral care in products such as toothpaste, mouthwash and the like; materials such as ceramics; delivery systems for pesticides including insecticides; delivery of herbicides, fungicides, and other agricultural products, and paints, and various chemical or polymer suspensions. One particular example is an industrial wash fluid, containing oxidizing or bleach agents, which demand strong and stable suspension systems.

The stabilizer of the present invention may be used in a variety of food products including emulsions, beverages, sauces, soups, syrups, dressings, films, dairy and non-dairy milks and products, frozen desserts, cultured foods, bakery fillings, and bakery cream. It may also be used for the delivery of flavoring agents and coloring agents. The edible food products can additionally comprise diverse edible material and additives, including proteins, fruit or vegetable juices, fruit or vegetable pulps, fruit-flavored substances, or any combination thereof. These food products can also include other edible ingredients such as, for example, mineral salts, protein sources, acidulants, sweeteners, buffering agents, pH modifiers, stabilizing salts, or a combination thereof. Those skilled in the art will recognize that any number of other edible components may also be added, for example, additional flavorings, colorings, preservatives, pH buffers, nutritional supplements, process aids, and the like. The additional edible ingredients can be soluble or insoluble, and, if insoluble, can be suspended in the food product. Routine adjustment of the composition is fully within the capabilities of one having skill in the art and is within the scope and intent of the present invention. These edible food products can be dry mix products (instant sauces, gravies, soups, instant cocoa drinks, etc.), low pH dairy systems (sour cream/yogurt, yogurt drinks, stabilized frozen yogurt, etc.), baked goods, and as a bulking agent in non-aqueous food systems and in low moisture food systems.

Juices suitable for incorporating the stabilizer composition include fruit juices (including but not limited to lemon juice, lime juice, and orange juice, including variations such as lemonade, limeade, or orangeade, white and red grape juices, grapefruit juice, apple juice, pear juice, cranberry juice, blueberry juice, raspberry juice, cherry juice, pineapple juice, pomegranate juice, mango juice, apricot juice or nectar, strawberry juice, and kiwi juice) and vegetable juices (including but not limited to tomato juice, carrot juice, celery juice, beet juice, parsley juice, spinach juice, and lettuce juice). The juices may be in any form, including liquid, solid, or semi-solid forms such as gels or other concentrates, ices or sorbets, or powders, and may also contain suspended solids. In another embodiment, fruit-flavored or other sweetened substances, including naturally flavored, artificially flavored, or those With Other Natural Flavors ("WONF"), may be used instead of fruit juice. Such fruit flavored substances may also be in the form of liquids, solids, or semi-solids, such as powders, gels or other concentrates, ices, or sorbets, and may also contain suspended solids.

Proteins suitable for the edible food products incorporating the stabilizer compositions include food proteins and amino acids, which can be beneficial to mammals, birds, reptiles, and fish. Food proteins include animal or plant proteins and fractions or derivatives thereof. Animal derived proteins include milk and milk derived products, such as heavy cream, light cream, whole milk, low fat milk, skim milk, fortified milk including protein fortified milk, processed milk and milk products including superheated and/or condensed, sweetened or unsweetened skin milk or whole milk, dried milk powders including whole milk powder and Nonfat Dry Milk (NFDM), casein and caseinates, whey and whey derived products such as whey concentrate, delactosed whey, demineralized whey, whey protein isolate. Egg and egg-derived proteins may also be used. Plant derived proteins include nut and nut derived proteins, sorghum, legume and legume derived proteins such as soy and soy derived products such as untreated fresh soy, fluid soy, soy concentrate, soy isolate, soy flour, and rice proteins, and all forms and fractions thereof. Food proteins may be used in any available form, including liquid, condensed, or powdered. When using a powdered protein source, however, it may be desirable to pre-hydrate the protein source prior to blending with stabilizer compositions and juice for added stability of the resulting beverage. When protein is added in conjunction with a fruit or vegetable juice, the amount used will depend upon the desired end result.

It should also be noted that the food/beverage compositions may be processed by heat treatment in any number of ways. These methods may include, but are not limited to, Low Temperature Long Time (LTLT), High Temperature Short Time (HTST), Ultra-High Temperature (UHT) and Extended Shelf Life (ESL) processes. These beverage compositions may also be retort processed, either by rotary retort or static retort processing. Some compositions, such as juice-added or natural or artificially flavored soft drinks may also be cold processed. Many of these processes may also incorporate homogenization or other high shear/high compression methods. There may also be co-dried compositions, which can be prepared in dry- mix form, and then conveniently reconstituted for consumption as needed. The resulting beverage compositions may be refrigerated and stored for a commercially acceptable period of time. In the alternative, the resulting beverages may be stored at room temperature, provided they are filled under aseptic conditions.

The described compositions can act as stabilizers are suitable for use in the beverage industry. The compositions, after drying to powder form, can be mixed with an aqueous solution to form a colloidal mixture that, in some embodiments, can maintain its colloidal properties for a long period of time. Some of the edible food products are beverages, protein and nutritional beverages, mineral fortified beverages, dairy-based beverages, and non-dairy based beverages including, but not limited to, those that are heat treated, for example, by pasteurization, ultra-pasteurization, or retort processes. The typical concentrations of the stabilizer of the present invention used in the above beverage products can range from 0.05% to about 3.5% by wt. of total products, and in some instances 0.2 to 2.0% by wt. of total products

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

The MCC wetcakes used in these Examples were obtained via hydrochloric acid hydrolysis of a prehydrolyzed hardwood pulp (Sulfatate™, available from Rayonier Inc.). The wetcakes are prepared for attrition by mixing aggregated MCC at 43.05% wt. solids, with a polysaccharide and an acid, as follows:

All ingredients were mixed in a 12-quart bowl on a Hobart A120 mixer (Model No. ML 38904). The wetcake was first loaded in the Hobart mixer bowl. The beater/paddle was then assembled to rotate at lowest setting. Other ingredients such as acids and/or salts were also added to the mixer. The beater/paddle rotation speed was progressively increased to the highest setting until a visually uniform admixture was achieved. This typically took 3-5 minutes. Then, polysaccharides were mixed in for 3-5 minutes in the Hobart mixer bowl. Afterwards, the mixed admixture was fed into a 2" Readco extruder from Readco Kurimoto, LLC. Three passes were normally conducted, unless specified. The extrusion performance was monitored by reading the torque on an attached amperage meter; measuring the temperature of extrudate; and, observing the texture of extrudates. Higher amperage meter readings, hotter extrudate, and firmer extrudate, indicated more effective co-attrition. A simple examination of the extrudates may be performed by measuring the viscosities of the wetcake mixtures slurried in di-water (deionized water) and by studying dispersion of MCC crystals in the slurries microscopically. Ultimately, the exemplary extrudates were dried into a powder form by slurring in di-water before being spray dried in a Stork-Bowen 3' spray drier with an atomizing nozzle, a heating temperature of 225° C., and collecting temperature of 120° C.-130° C. To produce neutral pH powders, 4% sodium hydroxide (NaOH) solution was used to neutralize the slurries before drying.

Sample Dispersion Preparation and Viscosity Measurements:

Sample dispersions for initial and 24-hour viscosity measurements were prepared in a 700G Waring blender (Model WF2212112) by Waring Commercial with a glass 4 cup bowl size. The speed of rotation blade was adjusted by an autotransformer. Each dispersion sample size was set at 600 g. Samples were introduced to the center of a di-water vortex at approximately 30 volts. After loading samples, the lid was placed on the bowl. The pre-mixing took about 15 seconds. The voltage of autotransformer was then increased to 115 volts for 2 minutes. The viscosity of the prepared sample dispersions was measured promptly using a Brookfield RV viscometer at 20 rpm. This viscosity measurement is termed as initial viscosity. After the initial viscosity measurements, the dispersions were allowed to sit on a bench without disturbance for 24 hours in a closed jar and thereafter the viscosities were measured again.

Dynamic Moduli Measurements of Sample Dispersions:

Dynamic moduli were measured with a TA-Instruments ARES-RFS3 using a 50 mm parallel geometry with a 1.8 mm gap size at 20° C. Strain tests were performed from 0.1 to 100% strain at 1 Hz with a 5 minutes equilibration. The samples in the measurements were the same dispersions as those used for 24-hour viscosity measurements.

HTST (High Temperature Short Time) and UHT (Ultra High Temperature) Flavored Milk Evaluation:

The flavored milk used in the evaluation is chocolate low fat milk with test formulation given in the table below.

TABLE 1

| Formulation @ 3.0-3.5% wt. Protein, 1.0-1.5% wt. Fat Content | % wt. wt. |
|---|---|
| Sugar | 7.5 |
| Cocoa Powder | 0.9 |
| Sample Stabilizer | Various |
| Fresh Milk, 1.0% wt. Fat | Add to 100 |

HTST Evaluation Method: Dry stabilizer and cocoa powder were blended together with sugar and then mixed for approximately 30 minutes in fresh milk using a medium shear propeller mixer (e.g., type Heidolph RZR 2020 or equivalent)

The milk solution was heated to 85° C. and pasteurized for 15 s. The treated milk solution was passed through a Niro Soavi homogenizer (or equivalent) with a two-stage pressure of 2500 psi at first stage followed by 500 psi at second stage. After homogenization, part of the solution was filled into autoclavable bottles and retorted at 121° C. for 1min. Once the retort process was completed, the chocolate milk was cooled immediately in an ice bath to 20-25° C. (retort process)

The remaining chocolate milk was cooled to 20-25° C. and placed into sterile plastic bottles (pasteurization process). The bottled samples from the retort process were stored at room temperature; the bottled samples from the pasteurization process were stored at refrigerated temperature (4° C.). The pH and viscosity of the samples were measured. After one week, visual inspection was conducted on the samples stored at refrigeration and ambient temperatures.

UHT Evaluation Method:

The samples (6 L batch size) were prepared, as follows:

i. A stabilizer sample was dry-blended with cocoa powder and sugar.

ii. The dry-blend was added to milk and mixed at medium shear with a propeller mixer to visually uniform mixture for approximately 30 minutes.

iii. The chocolate milk solution was pre-heated to 185° F. (85° C.) in first-stage pre-heating tubes, then heated to an UHT temperature of 284° F. (140° C.) and held for 6 seconds.

iv. Downstream homogenization was performed at total pressure of 2500 psi (2000 psi and then 500 psi).

v. Chocolate milk was then cooled immediately to <20° C. and filled in a sterile Nalgene bottle in a clean fill hood. The samples were evaluated after 3 months storage under both ambient (20-25° C.) and refrigeration (4° C.) conditions. Viscosity, pH, phase separation, flow properties, flocculation and dusting level were measured and/or characterized.

Example No. 1-6

Alginate

The alginate used was Manucol DM available from FMC, a product of a low gel strength alginate. It has 1% wt. solution viscosity of 150-300 cP at 20° C. with Brookfield LV viscometer at 60 rpm. The ratio of MCC to alginate was 85/15 by solids content. The amount of acid in each sample was 5% wt. based on the water content of the MCC wetcake. For instance, if 1000g MCC wetcake was used, 75.97g Manucol DM was (=(15/85)×1000×43.05% wt.) and 28.48g acid was (=5% wt.×1000×(100% wt. ×43.05% wt.)) in the mixture. Three passes of the mixture of the MCC/alginate and acid wetcakes were made through the Readco extruder.

TABLE 2

| Attrition Aid | Use level | Amperage reading of Readco extruder at third pass | Observation to post-attrite wetcake | Redispersion at 2.6% wt. of total solid | Observation to dispersion after 24-hour |
|---|---|---|---|---|---|
| None | | 4.0 | Soft/slippery | No test | |
| Citric acid | 5% wt. | 5.0 | Firm | Dispersed | Stable |
| Malic acid | 5% wt. | 5.0 | Firm | Dispersed | Stable |
| Tartaric acid | 5% wt. | 5.0 | Firm | Dispersed | Slight phase separation |
| 20% wt. Nitric acid | 5% wt. | 5.0 | Firm | Dispersed | Stable |
| 20% wt. Hydrochloric acid | 5% wt. | 5.2 | Firm | Dispersed | Stable |

Comparative Examples No. 1-6

Alginate

The same combinations of MCC/alginate were used as in Examples No. 1-6. Instead of acids, monovalent and divalent metal salts were used.

TABLE 3

| Attrition Aid | Use level | Amperage reading of Readco extruder at third pass | Observation to post-attrite wetcake | Redispersion at 2.6% wt. of total solid | Observation to dispersion after 24-hour |
|---|---|---|---|---|---|
| Sodium chloride | 5% wt. | 4.5 | No slippery | Dispersed | Flocculation |

TABLE 3-continued

| Attrition Aid | Use level | Amperage reading of Readco extruder at third pass | Observation to post-attrite wetcake | Redispersion at 2.6% wt. of total solid | Observation to dispersion after 24-hour |
|---|---|---|---|---|---|
| Sodium acetate | 5% wt. | 4.0 | Soft/slippery | No test | |
| Sodium carbonate | 5% wt. | 4.2 | Slippery | Dispersed | Flocculation |
| Sodium gluconate | 5% wt. | 4.0 | Soft/slippery | No test | |
| Sodium sulfate | 5% wt. | 4.0 | Soft/slippery | No test | |
| Zinc sulfate | 5% wt. | 6.0 | Firm | Dispersed | Phase separation |

TABLE 4-continued

| Alginate in MCC/alginate (=85/15) | Attrition Aid | Use level | Initial viscosity (cP) | 24-hour viscosity (cP) | pH |
|---|---|---|---|---|---|
| | Tartaric acid | 5% wt. | 400 | 646 | 3.41 |
| | 20% wt. Nitric acid | 5% wt. | 5140 | 5280 | 4.09 |
| | 20% wt. Hydrochloric acid | 5% wt. | 1365 | 2635 | 3.89 |
| Alginate Z** | Citric acid | 5% wt. | 4040 | 2400 | 3.88 |

*MCC/Manucol LD: amperage reading of Readco extruder at third pass = 4.3 with baseline of 4.1
**MCC/Alginate Z: amperage reading of Readco extruder at third pass = 4.4 with baseline of 4.3

Example No. 16-24

Alginate

TABLE 5

| Sample | Attrition Aid | Use level | Concentrations of dispersions | Initial viscosity (cP) | 24-hour viscosity (cP) | G' @ 1% of strain | pH | Comment |
|---|---|---|---|---|---|---|---|---|
| MCC/Manucol DM = 85/15 | None | | 2.6% wt. | 440 | 462 | | 5.91 | Wet blending |
| | Malic acid | 4% wt. | 2.6% wt. | 2780 | 3050 | | 3.8 | Unneutralized |
| | Citric acid | 4% wt. | 2.6% wt. | 3410 | 3500 | | 3.87 | Unneutralized |
| | Malic acid | 4% wt. | 2.6% wt. | 1102 | 1146 | | 6.33 | Neutralized |
| | Citric acid | 4% wt. | 2.6% wt. | 1198 | 1244 | | 5.9 | Neutralized |
| | Malic acid | 4% wt. | 1.2% wt. | 177 | 808 | 6.9 | 4.05 | Unneutralized |
| | Citric acid | 4% wt. | 1.2% wt. | 487 | 1465 | 18.9 | 4.09 | Unneutralized |
| | Malic acid | 4% wt. | 1.2% wt. | 204 | 242 | 7.1 | 6.02 | Neutralized |
| | Citric acid | 4% wt. | 1.2% wt. | | 316 | 9.7 | 5.97 | Neutralized |

Example No. 7-15

Alginate

The dispersion viscosity measurements were performed on 2.6% wt. dispersions from extrudates without drying. In these examples, the polysaccharide, Manucol LD, is a low gel strength alginate from FMC having 1% wt. solution viscosity of 4-12 cP at 20° C. measured with a Brookfield LV viscometer at 60 rpm. Alginate Z is an alginate sourced from Lessonia nigrescens having 1% wt. solution viscosity of 520 cP at 20° C. measured with a Brookfield LV viscometer at 60 rpm.

TABLE 4

| Alginate in MCC/alginate (=85/15) | Attrition Aid | Use level | Initial viscosity (cP) | 24-hour viscosity (cP) | pH |
|---|---|---|---|---|---|
| Manucol LD* | Malic acid | 4% wt. | 860 | 1770 | 3.79 |
| Manucol DM | Malic acid | 4% wt. | 3185 | 4680 | 3.73 |
| | Citric acid | 4% wt. | 5060 | 5450 | 3.84 |
| | Citric acid | 5% wt. | 1266 | 1652 | 3.69 |
| | Malic acid | 5% wt. | 1482 | 2150 | 3.67 |

Example No. 25-28

Alginate

Examples are MCC/Manucol DM=85/15 with 5% wt. malic acid or citric acid. The dispersions were prepared using a Silverson L4RT high shear mixer at 8500rpm for 5 minutes. The dynamic moduli were measured on the dispersions stored on bench for 2 weeks.

TABLE 6

| Attrition aid | Concentration (% wt.) | Storage time in weeks | G' @ 1% strain | pH |
|---|---|---|---|---|
| Citric acid | 1.2 | 0 | 6.5 | 4.00 |
| | | 1 | 9.5 | 3.98 |
| | | 2 | 12.2 | 3.99 |
| | 2.6 | 0 | 111.8 | 3.82 |
| | | 2 | 162.7 | 3.85 |
| Malic acid | 1.2 | 0 | 2.1 | 3.82 |
| | | 1 | 3.2 | 3.85 |
| | | 2 | 3.7 | 3.91 |
| | 2.6 | 0 | 30.4 | 3.73 |
| | | 2 | 47.3 | 3.80 |

Example No. 29

HTST Evaluation on Colloidal MCC/Alginate

Two neutral powder samples A and B of colloidal MCC/Manucol DM were made in a Readco extruder at,
A. MCC/Manucol DM=89/11 with 1% wt. citric acid, and
B. MCC/Manucol DM=89/11 without citric acid.

Sample A had 1030cP initial viscosity at 2.6% wt. and 1040cP of 24-hour viscosity. Sample B had 520cP of initial viscosity at 2.6% wt. and 525cP of 24-hour viscosity. For comparison of formulations with and without citric acid, HTST test samples were prepared, as described above in the section captioned "HTST (High Temperature Short Time) and UHT (Ultra High Temperature) flavored milk evaluation" by blending one of Samples A or B, with 150 ppm gellan HA, sugar, cocoa powder and low fat milk. The use level of the samples was 0.5% wt.

The blended HTST chocolate flavored low fat milk samples prepared with samples A and B were divided into a first group that was pasteurized and a second group of samples that was retorted, also as described above.

After one-week storage in refrigeration (4° C.) the pasteurized group was visually examined. Those samples prepared with Sample A showed slight phase separation and no cocoa powder sedimentation. Those samples prepared with Sample B showed partial cocoa powder sedimentation, with light brown color top phase separation at ⅔ of the height of bottle and dark brown color bottom phase separation at ⅓ of the height of bottle.

After one-week storage at ambient temperatures the retort group were visually examined. Those samples prepared with Sample A showed no cocoa powder sedimentation and almost no phase separation. Those samples prepared with Sample B showed no cocoa powder sedimentation with slight phase separation; however, there were many small chunks of gelled substance at the bottom of bottle.

Example No. 30

UHT Evaluation on Colloidal MCC/Alciinate

MCC/Manucol DM=85/15 with 4% wt. citric acid made through Readco extruder (see example No. 20).

A combination of MCC/Manucol DM at 0.35% wt. and gellan HA at 250 ppm was evaluated as a stabilizer in UHT low fat chocolate milk. After three months under refrigeration and ambient storage, there was no observation of cocoa sedimentation or gelation. As a comparison, with only 250 ppm gellan HA, there was observed low levels of dusting and no gelation of milk.

A combination of MCC/Manucol DM at 0.5% wt. and gellan HA at 150ppm as a stabilizer was also evaluated in UHT low fat chocolate milk. After three months in refrigeration and in ambient storage, there was no sedimentation and no gelation of milk. Only low levels of dusting were observed at the bottom of bottle in the ambient storage milk. As a comparison, heavy sedimentation layers were apparent in the chocolate milk stabilized with only 150 ppm gellan HA in both refrigeration and ambient storage.

Example No. 31

Alginic Acid

MCC/alginic acid (polysaccharide) was used in this example without other chemicals. During Readco attrition, the extrudate formed as moisturized mixture flakes. By directly dispersing in di-water, the mixture can be dispersed to form a thin dispersion at pH=3.69. For a duplicate dispersion, pH was adjusted with 4% wt. NaOH solution to 5.74. Both dispersions were observed to exhibit phase separation after 24 hours.

TABLE 7

| Amp. reading of Readco extruder at third pass | Observation to post-attrited wetcake | Re-dispersion at 2.6% wt. of total solid | Initial viscosity (cP) | 24-hour viscosity (cP) | Observation to dispersion after 24-hour | pH |
|---|---|---|---|---|---|---|
| 5.0* | Moisture powder | Dispersed | 74.5 | No test | Phase separation | 5.74 |

*baseline of Readco extruder amperage reading = 4.3

Example No. 32

Alginate

In this example, a high gel strength alginate, Manugel GHB, from FMC was tested. The ratio of MCC to the alginate is 85/15. The citric acid at 5% wt. was employed as the attrition aid. The amperage reading of Readco extruder was 5.2 at third pass versus 4.3 without citric acid.

Colloidal MCCs with Other Polysaccharides

Examples No. 33-36

Karaya Gum

Several different viscosity grade karaya gums were tested with MCC/karaya =85/15 at 5% wt. citric acid. Citric acid worked very well to promote effective attritions on the low viscosity grade karaya gum. As viscosity of karaya gum increases, assistance to co-attrition from citric acid becomes less effective. The viscosity of MCC/karaya dispersions was measured at 2.6% wt.

TABLE 8

| Viscosity of karaya gum* (cP) | Attrition Aid | Amperage reading of Readco extruder at third pass (first pass) | Observation to post-attrite wetcake | Initial viscosity (cP) | 24-hour viscosity (cP) | pH |
|---|---|---|---|---|---|---|
| 240 | None | 4.3 (4.3) | Less sticky | 165 | 235 | |
| 240 | 5% wt. citric acid | 5.2 (4.4) | Firm | 300 | 380 | 6.59 |
| 900-1600** | 5% wt. citric acid | 4.5 (4.3) | Sticky | No test | No test | |
| 2700-3400 | 5% wt. citric acid | 4.2 (4.2) | Soft, very sticky | No test | No test | |

*1% wt. solution of karaya with Brookfield RV viscometer at 20 rpm
**see example No. 37

Example No. 37-39

Karava Gum

Examples were made with a karaya gum at 1329cP of 1% wt. solution viscosity. The ratio of MCC/karaya=85/15. Different acids were tested at 5% wt. of use level. The viscosity of MCC/karaya dispersions was measured at 2.6% wt.

TABLE 9

No. 40-46 Karaya Gum with Citric Acid and Comparative Salts

| Attrition Aid | Amperage reading of Readco extruder at third pass (first pass) | Initial viscosity (cP) | 24-hour viscosity (cP) | pH |
|---|---|---|---|---|
| Citric acid | 4.5 (4.3) | 600 | 540 | 6.30 |
| 20% wt. Nitric acid | 4.6 (4.3) | 440 | 410 | 5.99 |
| 20% wt. Hydrochloric acid | 4.7 (4.3) | 330 | 305 | 6.21 |

Example No. 47

CMC 12M31

Earlier work on co-attrition of MCC/CMC 12M31 =85/15 revealed soft and slippery mass, where CMC 12M31 is carboxymethyl cellulose at D.S.=1.2 and 2% wt. solution viscosity of 800-3, 100cP from Ashland. Three use levels of citric acid were tested on the MCC/CMC 12M31: 6% wt., 8% wt. and 10% wt. At 10% wt., soft mixture of MCC/CMC 12M31 was noticed in the Hobart mixer bowl. The mixture was subjected to extrusion in the Readco extruder, and showed no change from the baseline 4.0 amperage reading. The mixture turned tough and firm in a sealed container under ambient condition after approximately 16 hours. When it was again subjected to extrusion in the Readco extruder, the amperage reading immediately increased to above 6.0. Without pH adjustment, the extrudate was dispersible in di-water at a solid concentration of 2.6% wt., yielding pH =3.36. In a duplicate dispersion test, pH of di-water was first adjusted to basic with a dilute NaOH solution. The extrudate was then dispersed in di-water

TABLE 10

| Viscosity of karaya gum (cP) | Attrition Aid | Use level | Amperage reading of Readco mixer at third pass (first pass) | Observation to post-attrite wetcake | Re-dispersion at 2.6% wt. of total solid | Initial viscosity (cP) | 24-hour viscosity (cP) | Observation to dispersion after 24-hour | pH |
|---|---|---|---|---|---|---|---|---|---|
| 240 | None | | 4.3 (4.3) | Less sticky | Dispersed | 165 | 235 | Stable | |
| 240 | Citric acid | 5% wt. | 5.2 (4.4) | Firm, not sticky | Dispersed | 300 | 380 | Stable with little flocculation | 6.59 |
| 240 | Calcium chloride | 5% wt. | 4.6 (4.4) | Firm, less sticky | Dispersed | 45 | 60 | Unstable, flocculation | 6.23 |
| 240 | Zinc sulfate | 5% wt. | 4.7 (4.4) | Firm, less sticky | Dispersed | 35 | 50 | Unstable, flocculation | 6.86 |
| 2750 | None | | 4.2 (4.2) | Soft, sticky | No test | | | | |
| 2750 | Calcium chloride | 5% wt. | 4.2 (4.2) | Soft, sticky | No test | | | | |
| 2750 | Zinc sulfate | 5% wt. | 4.2 (4.2) | Soft, sticky | No test | | | | | resulting pH =6.24. The neutralized dispersion exhibited 212.5 cP of initial viscosity and 271 cP of 24-hour viscosity. At 6% wt. and 8% wt. of citric acid, the mixtures stayed soft and sticky after 24 hours at ambient temperatures. It was however found that elevate temperatures accelerated the transition from soft sticky mass to tough and firm texture. At 40° C., for instance, the transition required about 24 hours for the MCC/CMC 12M31 with 8% wt. of citric acid. A separate mixture of MCC/CMC 12M31 with 10% wt. of citric acid made with the Hobart mixer and then warmed at 40° C. in a sealed container for 24 hours also became tough and firm. However, warming at 40° C. for 24 hours was not enough for the mixture with 6% wt. citric acid to turn to tough and firm. Eventually, this particular mixture became tough and firm in a cool (around 4° C.) storage after several weeks.

Example No. 48

Soybean Polysaccharide

A mixture of MCC/Soybean polysaccharide=85/15 was successfully co-attrited with 5% wt. citric acid. At third pass, the amperage reading was 4.9. Comparatively, the amperage reading was 4.3 at first pass through Readco extruder.

Example No. 49

Xanthan Gum

With up to about 10% wt. citric acid, a mixture of MCC/xanthan=85/15 was not effectively co-attrited. The mixture stayed soft and sticky.

Example No. 50

Alginate with Citric Acid at A Reduced Concentration

The alginate used was Manucol DM. The ratio of MCC to alginate was 86/14 by solid. The amount of citric acid was 2.5% wt. based on the water content of the wetcake. Three passes of the mixture of the aggregate MCC, alginate and citric acid were made through the Readco extruder. The baseline amperage was 3.9. At the third pass, the amperage reading was 4.2. The 2.6% dispersion on the spray dried neutralized powder yielded 1088cP of initial viscosity and 1127cP of 24-hour viscosity with pH=6.29

More passes of the mixture through the Readco extruder were found to increase firmness of the extrudate (the MCC wetcake mixture with Manucol DM and citric acid). For instance, six passes were conducted. At the sixth pass, the amperage reading was higher than 5.0. The 2.6% dispersion on the spray dried neutralized powder yielded 3025cP of initial viscosity and 2750cP of 24-hour viscosity with pH=6.26.

The colloidal content measurements were conducted on the samples, which method is detailed below,
1. Make 1.2% dispersion of powder in 592.8g di-water by using a 700G Waring blender in a glass 4 cup bowl at 115 volts of the voltage of autotransformer for 2 minutes
2. Dilute the 1.2% dispersion with di-water until 0.286%
3. Weigh 30 g of the diluted dispersion into a weight boat and mark as boat A
4. Weigh 30 g of the diluted dispersion into a 50mL centrifuge tube
5. Repeat step no. 4 five times
6. Centrifuge (Eppendorf Centrifuge 5804R from Eppendorf AG, Hamburg, Germany) six centrifuge tubes containing the dispersions from steps no. 4 to no.5 at 8300rpm which is equivalent to 8857 rcf of g-force for 15 minutes
7. Collect supernatants from the six centrifuge tubes and weigh the same amount as step no. 3 into another weight boat and mark as boat B
8. Dry boats A and B at 57° C. for around 24 hours or until complete dry
9. Colloidal content is calculated as the weight ratio of tared weight from boat B to tared weight from boat A.

The colloidal content was obtained 19.75% on the sample made by passing the mixture of MCC wetcake, alginate and citric acid through the Readco extruder three times. On the sample made by passing the mixture of MCC wetcake, alginate and citric acid through the Readco extruder six times, the colloidal content was measured to be 70.39%.

The colloidal content is a characterization result to assess the particle size of the dispersions. Avicel® CL611 has, for example, the colloidal content of around 70%. The supernatants collected from its dispersion were measured with a Horiba LA-910 laser diffraction particle size analyzer, Kyoto, Japan to yield a particle size distribution between 0.044 μm and 1.151 μm with 0.110 μm of $D_{50}$. Thus, increase in the number of the attrition passes through the Readco extruder leads to a further reduction of particle size in the dispersions (19.75% versus 70.39% in colloidal contents).

Example No. 51

Alginate with Phosphoric Acid

At the same molar concentration as citric acid in Example 50, phosphoric acid was instead used. The alginate used was Manucol DM. The ratio of MCC to alginate was 86/14 by solid. The amount of phosphoric acid was 1.5% wt. based on the water content of the MCC wetcake. Three passes of the mixture of MCC wetcake, alginate and phosphoric acid were made through the Readco extruder. The baseline amperage was 3.9. The attrition amperage was recorded as 4.0 ($1^{st}$ pass), 4.0 ($2^{nd}$ pass) and 4.1 ($3^{rd}$ pass), respectively. The 2.6% dispersion on the spray dried powder after neutralization with 4% NaOH solution gave 1040 cP of initial viscosity and 1120 cP of 24-hour viscosity with pH=6.21.

What is claimed is:
1. An attrited colloidal MCC composition, comprising:
   a) MCC particles;
   b) an attrition agent which is an acid; and
   c) at least one polysaccharide selected from the group consisting of alginates, karayas, and mixtures thereof;
   wherein the MCC particles are at least partially coated directly with the at least one polysaccharide;
   wherein $D_{50}$ of at least 19% by volume of attrited colloidal MCC particles is about 0.110 microns; and
   wherein the attrited colloidal MCC composition is substantially free of carboxymethyl cellulose and salts containing multivalent ions.
2. The composition of claim 1 wherein
   a) the MCC particles comprise between about 40-91.99% wt. of the composition;
   b) the at least one polysaccharide comprises between about 8-50% wt. of the composition; and
   c) the attrition agent comprises between about 0.01-10% wt. of the composition.

3. The composition of claim 1 wherein the acid is selected from the group consisting of formic acid, acetic acid, propionic acid, butyric acid, valeric acid, tartaric acid, caproic acid, oxalic acid, lactic acid, malic acid, citric acid, benzoic acid, carbonic acid, hydrochloric acid, nitric acid, phosphoric acid, sulfuric acid, boric acid, hydrofluoric acid, and hydrobromic acid.

4. The composition of claim 1 wherein the $D_{50}$ of at least 25% by volume of the attrited colloidal MCC particles is about 0.110 microns.

5. The composition of claim 1 wherein the $D_{50}$ of at least 40% by volume of the attrited colloidal MCC particles is about 0.110 microns.

6. The composition of claim 1 wherein the $D_{50}$ of at least 70% by volume of the attrited colloidal MCC particles is about 0.110 microns.

7. A consumable product comprising the composition of claim 1.

8. The consumable product of claim 7 wherein the product is selected from the group consisting of foods, nutraceuticals, pharmaceuticals and cosmetics.

9. The composition of claim 1 wherein the at least one polysaccharide is alginate.

10. The composition of claim 1 wherein the acid is selected from the group consisting of malic acid, citric acid, tartaric acid, HCl, nitric acid and phosphoric acid.

11. The composition of claim 1 wherein the acid is selected from the group consisting of citric acid, HCl, nitric acid, phosphoric acid, and mixtures thereof.

12. The composition of claim 1 wherein at least about 70% by volume of the MCC particles is from about 0.110 microns to about 0.70 microns.

* * * * *